United States Patent [19]

Knüsel et al.

[11] 4,185,091

[45] Jan. 22, 1980

[54] USE OF AVILAMYCIN AS A FEED ADDITIVE

[75] Inventors: Fritz Knüsel, Zofingen; Jakob Nüesch, Arlesheim; Heinrich Peter, Binningen; Armel Rosselet, Fribourg, all of Switzerland

[73] Assignee: Ciba-Geigy Corporation, Ardsley, N.Y.

[21] Appl. No.: 908,499

[22] Filed: May 22, 1978

[30] Foreign Application Priority Data

May 26, 1977 [CH] Switzerland .......................... 6494/77

[51] Int. Cl.² ............................................. A61K 35/00
[52] U.S. Cl. .................................................... 424/118
[58] Field of Search .......................................... 424/118

[56] References Cited

PUBLICATIONS

Chemical Abstracts 56:13357(e) (1962).
Goldberg, Antibiotics, D. Van Nostrand Co. Inc., Princeton, N.J., 1959, pp. 178–179.

*Primary Examiner*—Jerome D. Goldberg
*Attorney, Agent, or Firm*—Frederick H. Rabin

[57] ABSTRACT

Feeds and feed additives for domestic animals and productive animals, which feeds and feed additives contain 1 to 500 ppm of avilamycin.

4 Claims, No Drawings

USE OF AVILAMYCIN AS A FEED ADDITIVE

DETAILED DISCLOSURE

The present invention relates to feeds and feed additives for productive animals.

In the rearing of fattening animals and other productive livestock it is desirable for economic reasons that the animals show the greatest possible increase in weight in the shortest possible time and with the least possible consumption of feed. It has already been suggested in this connection that there be added to the feed active substances which improve the animal's utilisation of feed by favourably affecting the intestinal flora. Substances of this type which have been used hitherto are antibiotics, such as penicillin, oxytetracycline, virginiamycin, etc., as well as sulphonamides and other antimicrobics.

Since antibiotics are used on a large scale in human and veterinary medicine as therapeutics for the treatment of diseases, the following aspects should be taken into consideration with regard to the choice of such a substance for use as a feed additive for productive animals:

the antibiotic should belong to those groups of substances which have no practical application in human medicine; the use of the antibiotic should not lead in the case of the treated animals to a selection of bacteria having cross-resistance to antibiotics used therapeutically; furthermore, the antibiotic should have on the one hand high affinity for fattening feedstuffs and for bacteria, and on the other hand only low affinity for animal organs, and should remain virtually unabsorbed; it should act principally against gram-positive germs, and should be able to fully develop this action even under anaerobic conditions. The aforementioned requirements are not satisfied or only partially satisfied by the antibiotics suggested hitherto for use as feed additives.

Feeds and feed additives are now suggested according to the invention which are characterised in that they contain avilamycin.

The feeds according to the invention contain 1 to 500 ppm of avilamycin. The feeds according to the invention preferably contain 1 to 200 ppm, particularly 5 to 50 ppm of avilamycin.

The feed additives according to the invention contain 0.1 to 25 percent by weight of avilamycin. The feed additives according to the invention preferably contain 1 to 5 percent by weight of avilamycin.

Avilamycin is an antibiotic of the orthosomycin group. It can be produced by aerobic cultivation of Streptomyces viridochromogenes A 23 575 (NRRL 2860) (see, e.g., German Pat. No. 1,116,864 or U.S. Pat. No. 3,131,126).

The feeds and feed additives according to the invention are excellently suitable for feeding productive animals, especially pigs and poultry (fowl, turkey-hens, geese, ducks and quail), and also calves and ruminants (cattle, sheep and goats). The feeds according to the invention are exceptionally suitable for fattening pigs.

The feeds according to the invention are produced by intimately mixing avilamycin with the fodder concerned. For this purpose, avilamycin can be used either as pure substance or as crude product.

To produce the feeds according to the invention, it is advantageous to firstly prepare a premix containing, depending on the desired final concentration in the finished feed, 0.1 to 25% by weight, preferably 1 to 5% by weight, of avilamycin. These premixes constitute the feed additives according to the invention.

The feed additives according to the invention are obtained by intimately mixing pure or crude avilamycin with a suitable carrier. Suitable carriers in a premix of this kind are organic and/or inorganic substances which have good mixing properties and good compatibility with the feed being used. Carriers which are suitable are, for example, maize flour, low-grade wheat flour, dried grain swill, soya-bean flour, calcium carbonate, calcium phosphate, bolus alba, etc. In many cases, the crude avilamycin produced in the manner described above can be used directly as premix. In certain cases, for example in the production of milk substitute for calves, it is expedient to formulate the premix as a wettable powder or soluble powder.

A feed (feedstuff) according to the invention is prepared by diluting the premix with the other feed constituents until the desired final concentration of avilamycin in the finished feed is obtained. An advantageous procedure comprises first further diluting the avilamycin premix with a feed constituent to be contained in the final feed, and then adding the other necessary feed constituents. By this means is obtained a particularly homogeneous distribution of avilamycin in the finished feed. This can also be obtained by first homogeneously mixing the avilamycin premix with the mineral substance/trace element/vitamin premix necessary for the finished feed, and to subsequently work up the resulting mixture with the main feed constituents to give the finished feed.

The content of avilamycin in a finished feed according to the invention can vary within the limits of 1 to 500 ppm, depending on whether the feed is used as a sole feed or only as a supplementary feed. A sole feed according to the invention contains avilamycin in amounts of 1 to 200 ppm, preferably 5 to 50 ppm. In the case of a supplementary feed, for example in the case of feeding fodder concentrate and hay and/or silage for fattening cattle, or fodder concentrate and silage for fattening pigs, and feeding protein concentrate and grain feed in the keeping of laying hens, the avilamycin concentration is to be increased according to the proportion of supplementary feed. The content of avilamycin in the supplementary feed can be up to 500 ppm, depending on the ratio of supplementary feed to basic feed. Where avilamycin is used in the feeding of ruminants, it can moreover be advantageous to choose a formulation which renders possible an undisturbed passage through the rumen. This can be effected for example by coating or by the known rumen-by-pass methods.

By virtue of their content of avilamycin, which has a harmonising effect on the intestinal flora, the feeds according to the invention can be extensively used, which leads to an accelerated growth of the animals. The advantageous action of avilamycin is such that on the one hand it suppresses the clostridia and enterococci which are known to be toxin-formers, whilst simultaneously preserving the lactobacilli, but on the other hand it avoids any excessive development of the gram-negative coliform flora occurring at the expense of clostridia and enterococci. In this manner there is obtained an equilibrium between lactobacilli and coli forms in the intestines, which is essential for the maintenance of a normal physiological intestinal flora. Furthermore, avilamycin has a high affinity for fattening fodder, celluose and bacteria. On the other hand, the binding of the avilamycin to animal organs is slight, so that consequently an undesirable absorption of the avilamycin is largely avoided. Avilamycin produces under anaerobic conditions a greater effect than in the presence of oxygen, and acts exclusively against gram-positive germs. Gram-negative germs, especially enterobacteriaceae, are not inhibited by avilamycin. There occurs therefore no influencing of the resistance conditions in the enterobacteriaceae flora, which contains the R factor, of the intestines of productive animals. In addition, there is no therapeutic use for avilamycin in human medicine. There moreover exists no cross-resistance between avilamycin and antibiotics which are important in human medicine, such as dihydrostreptomycin, neomycin, benzyl penicillin, erythromycin, oxytetracycline, chloramphenicol and novobiocin.

The production and use of the feeds and feed additives according to the invention are further illustrated by the following Examples.

EXAMPLE 1

Production of avilamycin (a) By means of aerobic cultivation of Streptomyces viridochromogenes A 23575 (NRRL 2860) in a sterilised nutrient medium, which contains per liter of water 20 g of meat flour, 20 g of malt extract and 10 g of calcium carbonate, there is produced at pH 7 with an incubation time of 24 hours a culture solution containing avilamycin. After fermentation is finished, the aqueous solution containing the avilamycin is separated by filtration from the mycelium and other solid constituents, and the filtrate is extracted with chloroform. Avilamycin is precipitated from the concentrated chloroform extract by the addition of petroleum ether. The crude avilamycin obtained in this manner is in the form of a powder which is slightly yellowish-brown in colour and which contains about 50% by weight of avilamycin. It can be used directly as a feed additive. Colourless crystals are obtained by crystallisation of the crude product from acetone/ether or acetone/water.

(b) To produce a commercial crude avilamycin, the fermentation solution containing avilamycin can be processed as follows: The culture solution produced as described under (a) is homogenised with the aid of a Dispax apparatus, and dried in a spray dryer, with two-component nozzles, in a parallel flow. The inlet temperature of the heated air is 180° C. The crude avilamycin, mixed with nutrient solution and cell constituents, is obtained in the form of a fine, light-coloured and virtually odourless powder, which can be used directly as a feed additive. The content of avilamycin in the spray-dried product is ascertained by extraction with chloroform or ethyl acetate, and subsequent microbiological or thin-layer-chromatographical determination.

EXAMPLE 2

(a) Production of a feed additive 98 kg of low-grade wheat flour and 2 kg of crude avilamycin (produced according to Example 1) are intimately mixed in a mixer and subsequently ground. There is obtained in this manner a feed additive containing 1% by weight of avilamycin.

(b) Production of a sole feed for fattening poultry 0.2 kg of the feed additive produced according to (a) is mixed with 100 kg of a poultry feed consisting of

| maize | | 26.7 | % by weight |
|---|---|---|---|
| wheat | | 21.2 | % by weight |
| barley | | 18.2 | % by weight |
| grass flour | | 1.2 | % by weight |
| soyabean meal | (44 %) | 16 | % by weight |
| fish flour | | 7.2 | % by weight |
| meat flour | | 5.0 | % by weight |
| beef tallow | | 2.0 | % by weight |
| dicalc. phosphate, | | 0.7 | % by weight |
| calcium carbonate, | | 0.8 | % by weight |
| sodium chloride (iodinated) | | 0.4 | % by weight |
| methionine DL-98 | | 0.1 | % by weight |
| vitamins + trace elements | | 0.5 | % by weight |

There is obtained in this manner a poultry sole feed containing about 20 ppm of avilamycin.

EXAMPLE 3

(a) Production of a feed additive 49 kg of calcium carbonate and 1 kg of crude avilamycin (produced according to Example 1) are intimately mixed in a mixer, and subsequently ground. In this manner is obtained a feed additive according to the invention, which contains 1% by weight of avilamycin.

(b) Production of a sole feed for fattening poultry 100 g of the feed additive produced according to (a) is mixed with 100 kg of a poultry sole feed consisting of

| maize | | 30.3 | % by weight |
|---|---|---|---|
| wheat | | 27.0 | % by weight |
| soyabean meal | (44 %) | 26.0 | % by weight |
| fish flour | | 5.0 | % by weight |
| beef tallow | | 5.0 | % by weight |
| dicalc. phosphate | | 0.8 | % by weight |
| calcium carbonate | | 0.5 | % by weight |
| sodium chloride (iodinated) | | 0.3 | % by weight |
| methionine DL-98 | | 0.1 | % by weight |
| vitamins + trace elements | | 0.5 | % by weight |

There is obtained in this manner a poultry sole feed containing about 10 ppm of avilamycin.

EXAMPLE 4

(a) Production of a feed additive 10 kg of crude avilamycin (produced according to Example 1) and 90 kg of maize flour are mixed together and subsequently ground to obtain a feed additive containing 5% by weight of avilamycin.

(b) Production of a pig-fattening feed

By mixing 0.25 kg, 0.5 kg, 1 kg and 2 kg of the feed additive obtained according to (a) into (in each case) one ton of a basic feed comprising

| 32.8 | % by weight of | maize |
|---|---|---|
| 23.0 | % by weight of | wheat |
| 15.0 | % by weight of | barley |
| 9.0 | % by weight of | soyabean meal (44%) |
| 4.0 | % by weight of | fish flour |
| 6.0 | % by weight of | meat flour |
| 1.8 | % by weight of | beef tallow |
| 1.0 | % by weight of | oat chaff |
| 5.0 | % by weight of | wheat bran |
| 0.5 | % by weight of | dicalc. phosphate |
| 0.9 | % by weight of | calcium carbonate |
| 0.5 | % by weight of | sodium chloride (iodinated) |
| 0.5 | % by weight of | vitamins + trace elements, | there are obtained pig feeds containing respectively 12.5 ppm, 25 ppm, 50 ppm and 100 ppm of avilamycin.

EXAMPLE 5

Poultry-fattening Test

The effect of avilamycin on the growth and on the feed utilisation of day-old chicks (Hubbard) is tested in a test lasting two weeks. The basic feed used is an experimental stress diet containing a high proportion of white beans. A diet of this kind leads to a retarded growth and to an inferior feed utilisation compared with the growth and feed utilisation resulting from a normal diet. This depression can however be largely eliminated by the addition of substances having a growth-promoting action (see Fernandez et al., Poult. Sci. 52, 1973, 2299–2305).

Avilamycin is added to the feed in a concentration of 180 ppm. A negative control test using a feed not containing avilamycin is concomitantly carried out. For each treatment, 4 groups (2 ♂ and 2 ♀) each of 10 day-chicks are installed in heatable cages. Feed and drinking water are available ad libitum. The weight of the chicks is determined at the commencement of the test and after 2 weeks (end of test), the chicks being weighed in groups, and the feed utilisation is calculated on the basis of the feed consumed in this period. The results obtained are shown in the following Table.

| Treatment - dose | | GROWTH | | FEED UTILISATION | |
|---|---|---|---|---|---|
| | | absolute g | % diff. with respect to neg. control | absolute kg | % diff. with respect to neg. control |
| neg. control | — | 137 | — | 1,95 | — |
| avilamycin | 180 ppm | 182 | + 32,8 | 1,71 | + 12,3 |

EXAMPLE 6

Poultry-fattening Test

The growth-promoting action of avilamycin is tested in a test lasting 4 weeks. The employed feed containing avilamycin is the diet with 20 ppm of avilamycin, produced according to Example 2. The feed is available ad libitum to the birds during the entire duration of the test.

For each of the two treatments (negative control/20 ppm of avilamycin) are used 8 groups (4 ♂ and 4 ♀) each consisting of 10 day-old chicks (Hubbard). The chicks are weighed in groups and installed in heated cages. Further weighings are made after 2 and 4 weeks (end of test). The consumption of feed is determined at the same time. The results of the test at the end of the test are shown in the following Table.

| Treatment - dose | | GROWTH | | FEED UTILISATION | |
|---|---|---|---|---|---|
| | | absolute g | % diff. with respect to neg. control | absolute kg | % diff. with respect to neg. control |
| neg. control | — | 634 | — | 1.782 | — |
| avilamycin | 20 ppm | 705* | + 11.2 | 1.713 | + 3.9 |

* = significantly different from neg. control P ≦ 0.05

EXAMPLE 7

Poultry-fattening Test

The growth-promoting action of avilamycin is tested in a test lasting 6 weeks. The employed feed containing avilamycin is the diet with 5 ppm of avilamycin, produced according to Example 3. The feed is available ad libitum to the birds during the entire duration of the test. As the negative control feed is used the same basic feed but without any additive at all. During the test, the birds are kept in Ehret batteries with cage heating. To each of the two treatments are assigned at random 12 groups (6 ♂ and 6 ♀) each consisting of 12 chicks. The following climatic conditions are maintained during the test:

| room temperature | | about 23° C. |
|---|---|---|
| cage temperature | 1st week | 32° C. |
| | 2nd + 3rd week | 30° C. |
| | 4th + 5th week | 26° C. |
| | 6th week | 23° C. |
| humidity 35 to 50%. | | |

For the evaluation of the test, the chicks are weighed before, during and at the end of the test, the consumption of feed being determined simultaneously. The test results are shown in the following Table.

| Treatment - dose | | GROWTH | | FEED UTILISATION | |
|---|---|---|---|---|---|
| | | absolute g | % diff. with respect to neg. control | absolute kg | % diff. with respect to neg. control |
| neg. control | — | 1402 | — | 1.904 | — |
| avilamycin | 5 ppm | 1447 | + 3.2 | 1.849* | + 2.9 |

* = significantly different from neg. control P ≦ 0.05

EXAMPLE 8

Pig-fattening Test

The growth-promoting effect of avilamycin on the pig is determined in a 4-week test, in which the results are compared with those obtained with a negative control feed. The employed feed containing avilamycin is the diet having 25 ppm of avilamycin, produced according to Example 4. All the animals receive the same basic feed before the commencement of the test. The identical basic feed is used as a negative control feed during the test. Feeding occurs with rationed amounts (meal form, ground feeding, water being available ad libitum). Each treatment is carried out with 12 piglets in three groups each of 4 animals, which have at the start of the test an average weight of 9.5 kg. The test results are shown in the following Table.

| | | | Days 0–28 | |
|---|---|---|---|---|
| Treatment | ppm | Initial weight in kg | DI and % diff. with respect to neg. control | FU and % diff. with respect to neg. control |
| 1 control | — | 9.12 | 236 | 1.97 |
| 3 avilamycin | 25 | 9.59 | 286 +21.2 | 1.74 +11.7 |

DI = daily increase in g
FU = feed utilisation (= kg of feed per kg of growth)

EXAMPLE 9

Pig-fattening Test

The growth-promoting action of avilamycin is determined, in a test lasting 8 weeks, with the feed produced according to Example 4, containing 12.5 ppm, 25 ppm, 50 ppm and 100 ppm of avilamycin, respectively. The identical basic feed without any additive is used as a comparison (negative control). The test is carried out with 2 batches staggered with respect to time. In the case of the first batch to be installed, 20 male (castrated) piglets and 20 female piglets are divided up, taking into account sex and origin, into 10 groups each of 4 animals. One group of male piglets and one group of female piglets are randomly subjected to one of 5 different treatments. The animals are kept and fed as described in Example 8. This test procedure is repeated 3 weeks later with a second batch of piglets, so that all together each treatment is tested on 2 groups of male animals and on 2 groups of female animals, each group consisting of 4 animals. The overall duration of the test amounts to 8 weeks. After 4 and 8 weeks, the average increase in weight and the utilisation of feed are determined. The results of the test are shown in the following Table.

| TREAT-MENT | ppm | Initial weight kg/ Age in days | Days 1–28 DI and % diff. with respect to neg. control | Days 1–28 FU and % diff. with respect to neg. control | Days 1–56 DI and % diff. with respect to neg. control | Days 1–56 FU and % diff. with respect to neg. control |
|---|---|---|---|---|---|---|
| control | — | 9.9/ 48 | 257 — | 1.88 — | 337 — | 2.07 — |
| avilamycin (A-23575-N-OK 56) | 12.5 | 10.5/ 48 | 263 +2.3 | 1.83 +2.7 | 348 +3.3 | 2.00 +3.4 |
| " | 25 | 10.9/ 48 | 268 +4.3 | 1.80 +4.3 | 358 +6.2 | 1.95 +5.8 |
| " | 50 | 10.3/ 48 | 281 +9.3 | 1.71 +9.0 | 371 +10.1 | 1.88 +9.2 |
| " | 100 | 9.7/ 48 | 282 +9.7 | 1.70 +9.6 | 365 +8.3 | 1.90 +8.2 |

DI = daily increase in g
FU = feed utilisation (=kg of feed per kg of growth)

The Examples in the foregoing show that avilamycin, when administered by way of the feed, has a clearly favourable effect on increase in weight and on feed utilisation both in the case of broilers and in the case of pigs.

EXAMPLE 10

Wettable Powder

A wettable powder which is suitable as an additive to be added to drinking liquids for domestic animals and productive animals, particularly to milk or milk substitute for calves, is obtained by mixing together 25 parts by weight of crude avilamycin (50%),
  5 parts by weight of sodium dibutylnaphthalenesulphonate (Tinovetin B),
  5 parts by weight of sodium lignin sulphonate,
  60 parts by weight of bolus alba, and
  5 parts by weight of silicic acid K 320 (highly dispersed silicic acid).

Instead of using bolus alba, it is also possible to use kaolin or Champagne chalk as carrier.

EXAMPLE 11

Soluble Powder

A soluble powder which is suitable as an additive for adding to drinking liquids for domestic animals and productive animals, particularly to milk or milk substitute for calves, is obtained by mixing together 40 parts by weight of crude avilamycin (50%),
  55 parts by weight of sodium chloride,
  5 parts by weight of silicic acid K 320 (highly dispersed silicic acid).

Instead of using sodium chloride, it is also possible to use sugar as a carrier.

We claim:
1. A method for promoting the growth of a domestic or productive animal which comprises administering to an animal in need of said promoting fodder containing from 1 to 500 ppm of avilamycin.
2. A method according to claim 1 in which the fodder contains from 1 to 200 ppm of avilamycin.
3. A method according to claim 2 in which the fodder contains from 5 to 50 ppm of avilamycin.
4. A method according to claim 1 in which the animal is selected from the group consisting of pigs, poultry and ruminants.

* * * * *